United States Patent [19]

Corella

[11] Patent Number: 4,579,221

[45] Date of Patent: Apr. 1, 1986

[54] PACKAGE, INSTRUMENTATION, SYSTEM AND METHOD FOR PACKAGING FLACCID ITEMS, FILAMENTS AND THE LIKE

[76] Inventor: Arthur P. Corella, 8166 Vanscoy Ave., North Hollywood, Calif. 91602

[21] Appl. No.: 723,353

[22] Filed: Apr. 15, 1985

[51] Int. Cl.⁴ .............................................. A61L 17/02
[52] U.S. Cl. ................................... 206/63.3; 206/388; 206/390; 206/63.5
[58] Field of Search ...................... 206/409, 390, 63.3, 206/63.5, 484, 388

[56] References Cited

U.S. PATENT DOCUMENTS

| | | | |
|---|---|---|---|
| 2,921,676 | 1/1960 | Carignan | 206/409 |
| 3,683,928 | 8/1972 | Kuntz | 206/409 |
| 3,921,802 | 11/1975 | Thompson | 206/390 |
| 4,014,433 | 3/1977 | Cerwin | 206/63.3 |
| 4,168,000 | 9/1979 | MacRitchie | 206/63.3 |
| 4,298,158 | 11/1981 | Hoppe et al. | 206/390 |

FOREIGN PATENT DOCUMENTS 516573 4/1921 France ............................. 206/63.3
184947 3/1922 United Kingdom ............... 206/63.3

Primary Examiner—Joseph Man-Fu Moy
Attorney, Agent, or Firm—Donald Diamond

[57] ABSTRACT

A peripherally sealed package (20) contains a bunched up portion (22a) of dental floss or other filament (22) with the outer ends (22b) of the floss or filament being disposed within and secured by sealed ends (26b and 26d) of the package. A notch (30) whose cut (30a and 30b) enables the package to be opened, uses a segment (34) of the package as a handle to draw the filament untangled and unknotted from the package. The package is formed using instrumentation including a feed tube (84) and a mandrel (86) which are concentrically positioned and relatively movable with respect to one another in timed movements. These movements, in conjunction with an accompanying sealer (54), holders (58, 72) and cutter (74a, 74b), draw an uncut length of filament (22) between two films (52a, 52b) of wrapping material, and bunch up a measured amount (22a) of the filament for deposit into an open-ended compartment (28) formed from the wrapping material.

17 Claims, 10 Drawing Figures

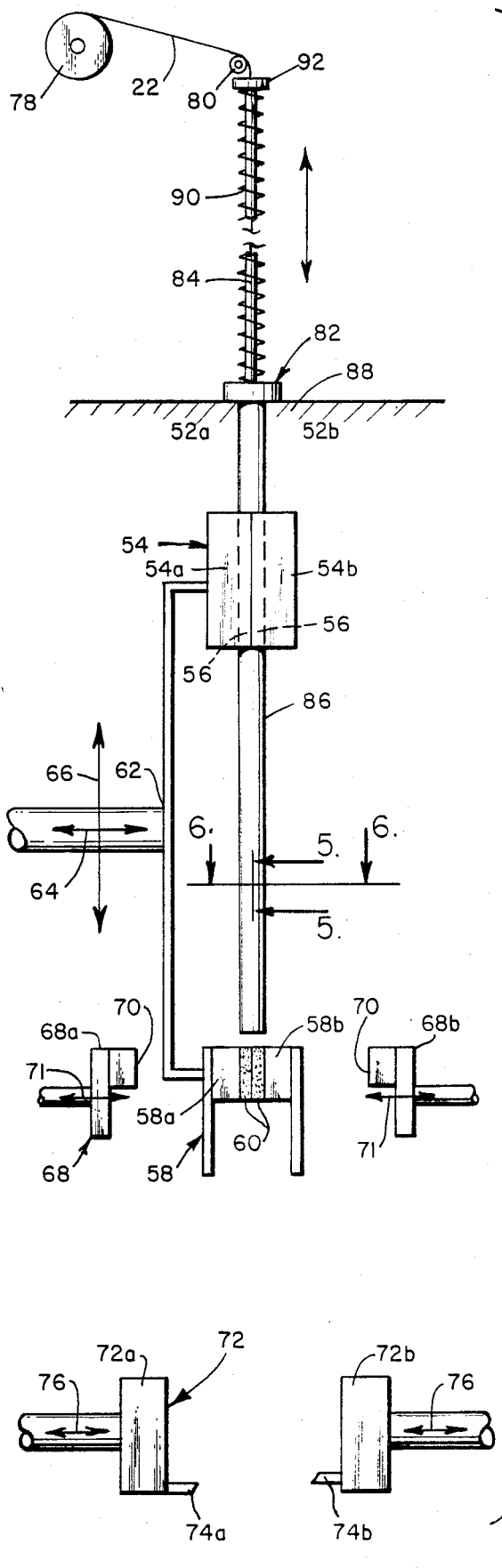
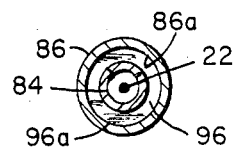
Fig. 6
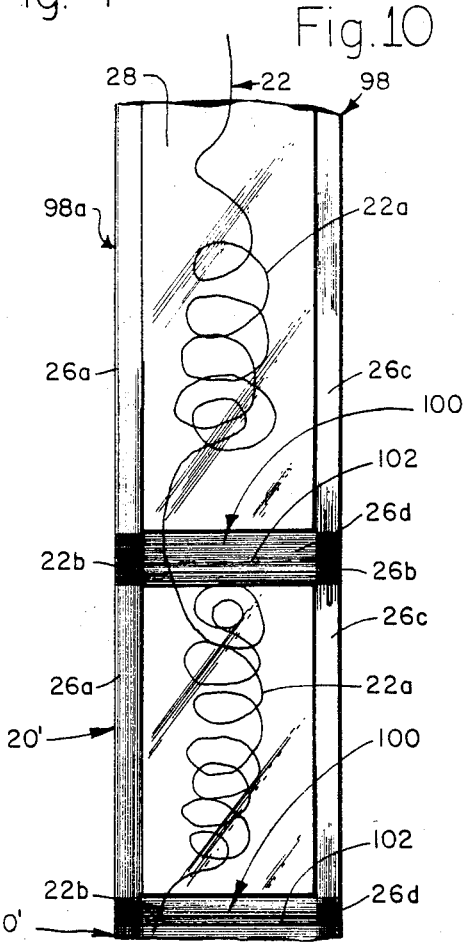
Fig. 5
Fig. 4
Fig. 10

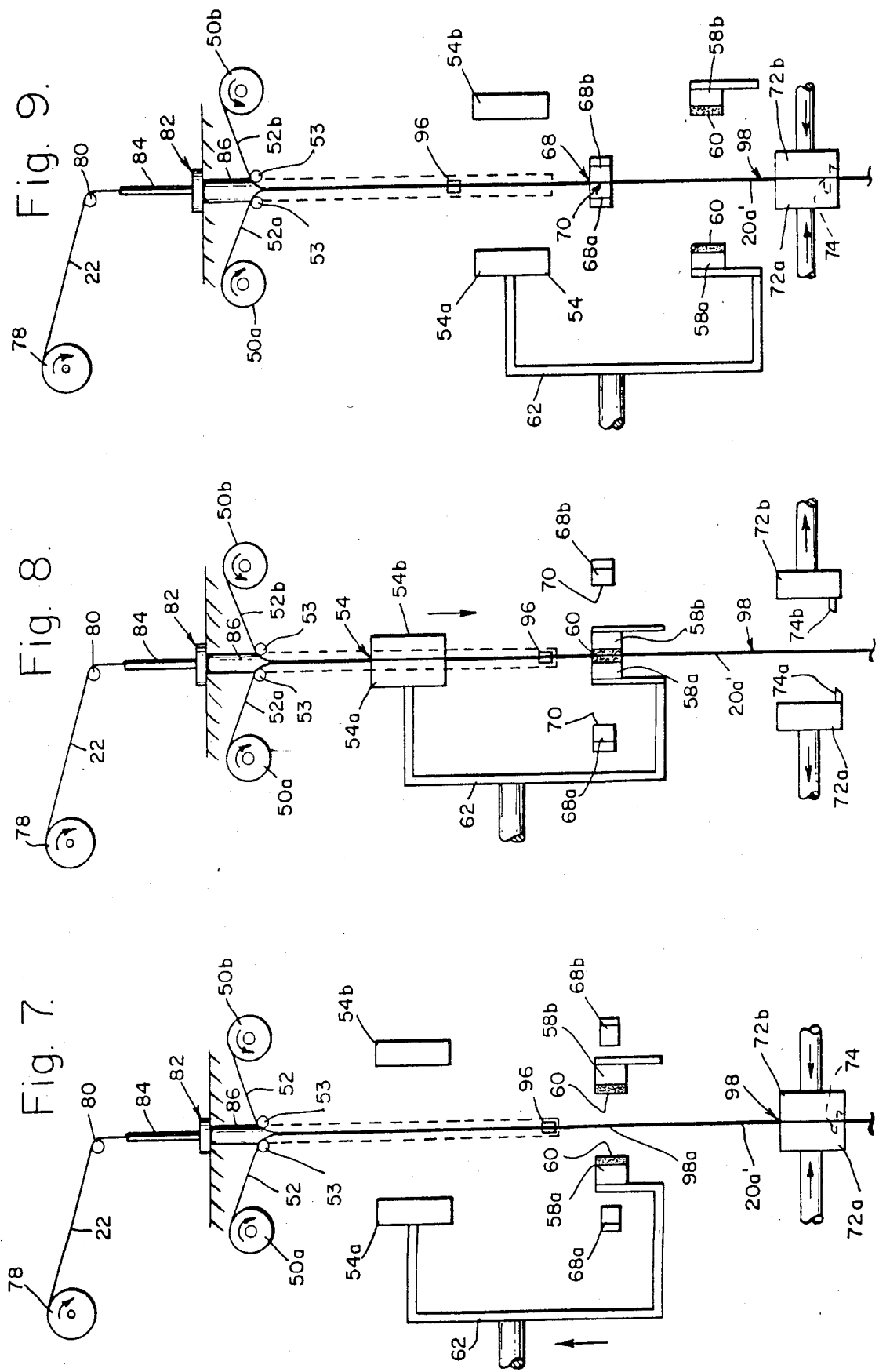

PACKAGE, INSTRUMENTATION, SYSTEM AND METHOD FOR PACKAGING FLACCID ITEMS, FILAMENTS AND THE LIKE

The present invention relates to a package, instrumentation, system and method in which flaccid items, filaments and the like are packaged from uncut supplies of the same, and from which the flaccid items can be packaged and withdrawn in an untangled and an unknotted condition.

Packaging of tablets, granular and liquid materials, and single relatively rigid times in sealed packages is a well-developed art. Because of their weight and substance, they are easily inserted or gravity dropped into the package enclosure. Such an enclosure may be fabricated from a continuous tube or a pair of sheets respectively sealed where the bottom or bottom and sides of the enclosure is to be formed and, for multiple package formation and filling, also intermediate the sides. The construction and use of equipment, and processing associated therewith, employed for such packaging are well known.

Conventional equipment and its use, however, are not altogether satisfactory when the items to be packaged are flaccid, such as filaments, wires, dental floss, and the like. In particular, conventional equipment presently is not automated at least for efficient packaging of such flaccid items. Accordingly, present practice is to stuff them into the enclosures to be formed into the packages. Whether or not efficiently performed, such practice militates against automation, and increases the number of rejects. Packaging costs, therefore, correspondingly increase.

The only known package for containing a flaccid item, specifically a thread, is one which encloses the thread with a bandage, e.g., a BAND-AIDS ® package, however, the thread therein is used solely to open the package, and is not the primary item intended to be packaged. In addition, because the thread is flaccid and not capable of self-support, it is necessary to adhere or otherwise secure the thread to one of the sides of the package, to provide the necessary support during manufacture of the package and its contained bandage.

Furthermore, opening of any package and removal and extraction of the filament or thread should be easy, without entanglement or knotting of the filament and without slippage of the thread from the package, as sometime occurs in the BAND-AIDS ® package.

SUMMARY OF THE INVENTION

The present invention avoids and overcomes these and other problems. Individual packages, which contain one or more flaccid items, depending on the customer's requirements, are sealed within an envelope. End portions of the flaccid item extend into and are sealingly entrapped within the seals. A cut extends partially into the seal and is positioned to separate an end of the flaccid item, along with a segment of the package seal in which it is entrapped, from the remainder of the package so that the segment acts as a handle by which the flaccid item may be withdrawn from the package in an untangled and an unknotted manner.

In a preferred embodiment, the packaging for enclosing a flaccid item comprises a fully sealed enclosure (i.e., a package) having a compartment and a sealed entry to the compartment. Continuous central and end portions of the flaccid item are respectively housed within the compartment and extend into and are sealed within the sealed entry near one or more corners of the package. A notch adjacent one of the item's end portions enables the seal to be torn in a controlled manner to remove the package's corener and the flaccid item entrapped therein so that the package is not only opened, but access is also provided to withdraw the flaccid item from the compartment. The corner thus operates as a handle for drawing the flaccid item evenly, and without entanglement and knotting, through the opening.

The packages are formed in a continuous manner from uncut lengths of the flaccid item and of the material to be formed into the package. The packaging material is taken from tubular stock formed generally as a sheath or from a pair of appropriately sealed sheets to provide a compartment with a sealed bottom and contiguous walls terminating at an open top. The flaccid item is positively fed or deposited into the compartment in an untangled manner by a feeding mechanism, rather than by gravity. The compartment is then sealed at its open end and cut into into individual packages.

The preferred feeding mechanism, when the flaccid item comprises a filament, includes a feed tube concentrically placed and slidable within a tubular mandrel. The feed tube is moved in sequential operations relative to the mandrel and with respect to compartment holding and sealing devices so that the packages are appropriately formed.

Several advantages are obtained therefrom. The flaccid item is deposited into, contained in, and removed from the package in an untangled and unknotted condition. A segment of the package is used as a handle in the removal. The packaging process is automated to eliminate unnecessary and otherwise relatively slow handling procedures. Thus, manufacturing costs are reduced. In conjunction therewith, the use of existing equipment is facilitated, to avoid the purchase of additional and possibly specially designed manufacturing equipment. Standard packaging materials can be used, so that new techniques for their handling and bonding or sealing are also avoided. As a consequence, advertising and/or labelling information may be incorporated, as is conventional with standard packaging.

Other aims and advantages, as well as a more complete understanding of the present invention, will appear from the following explanation of exemplary embodiments and the accompanying drawings thereof.

BRIEF DESCRIPTION OF THE DRAWINGS

FIG. 4 depicts a mechanism, apparatus or instrumentation for forming a package, such as shown in FIG. 1;

FIGS. 5 and 6 are cross-sectional views of the mechanism, apparatus or instrumentation of FIG. 4, taken respectively along lines 5—5 and 6—6 thereof;

FIGS. 7-9 are simplified views of the instrumentation shown in FIGS. 4-6 and the steps showing its use for forming such packages as are shown in FIGS. 1 and 2; and FIG. 10 is a side view of a portion of a package in process of formation, comprising an open-ended sheath and a completed package attached thereto prior to its separation from the sheath.

DESCRIPTION OF THE PREFERRED EMBODIMENTS

Figure 1:
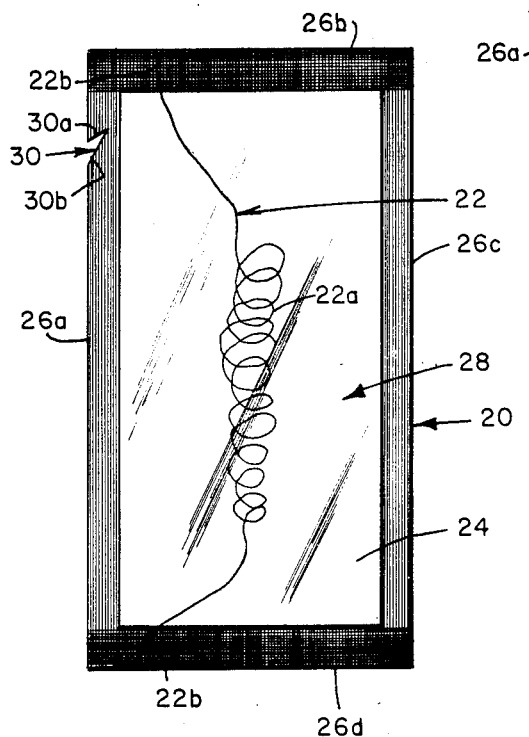
FIG. 1 illustrates a package configuration formed in accordance with a first embodiment of the present invention, in which a single length of flaccid item is sealed within an enclosure.

Accordingly, FIG. 1 illustrates a package or sealed enclosure 20, which contains a single continuously extending, uncut flaccid items 22. By flaccid, it is meant that item 22 has little or no rigidity or firmness and, therefore, is incapable of self-support; thus, when unsupported, it may be limp.

Flaccid item 22 comprises a central portion 22a and end or terminal portions 22b. Central portion 22a is bunched-up in an untangled manner, that i,s it is or may be massed together, but still be capable of being readily separated, so as to be free from being or becoming knotted. Such an untangled condition, as will be more fully explained below, permits the flaccid item to be extracted in an unknotted and untangled manner from its enclosure.

Representative flaccid items include filaments, for example, of thread or ribbon style dental floss, or of natural fiber, synthetic fiber, metallic wire, or of flat material with or without printing thereon, e.g., a paper with a message thereon, and combinations thereof. In addition, if desired, non-flaccid devices, such as a needle, may be packaged with the flaccid item within the package.

A typical package has a rectangularly-shaped flat configuration defined by a pair of large-surfaced, flat walls 24 which are sealed together at their perimeters as indicated by indicia 26a–26d to form a compartment 28 in which the flaccid item is contained.

As a further example of packaging techniques, package 20 may comprise a transparent wrapping to permit filament 22 to be seen or, at a minimum, translucent wrapping to permit display of a message.

The wrapping comprises any conventional, suitable material, composition or laminate, e.g., paper, plastic (such as polyethylene and MYLAR ® polyester film), aluminum foil, polyester-polyethylene, polyethylene-paper, and polyethylene-metal foil. In a laminate, the polyethylene forms the inner face and the paper or foil form the outer face of the walls. Polyethylene is preferred because it is readily heat-sealable to form the sealed peripheral walls. Paper or metal foil enables a message, illustration, and the like to be printed thereon.

As stated above, the wrapping for package 20 is shown as having seal 26a–26d extending fully around its periphery, in which seals 26a and 26c may be termed side seals and seals 26b and 26d may be termed top and bottom seals, respectively.

If package 20 were formed from tubular stock, it would have a single side seal at most and, therefore, be closed only with top and bottom seals, like seals 26b and 26d of FIG. 1, to form a sealed enclosure. These differences in the construction of the seals result both from the stock selected for the particular wrapping and from the machinery used in forming the wrappings into the packages. The wrapping for package 20 is taken from a pair of sheets, sealed together, for example, by use of the sealing die illustrated in FIG. 4.

Furthermore, it is not necessary that both end portions 22b of filament 22 extend into separate seals, such as top and bottom seals 26b and 26d of package 20; rather, any package may be so manufactured that the end portions extend through the same seal at the top or bottom of the package. Also, the filament end portions may terminate at the very edge of the package, or extend therebeyond.

An important feature of the present invention is a design which permits easy opening or rupture of any package and withdrawal of the filament in an untangled and unknotted manner from its sealed compartment. To this end, the filament is deposited into the package in an untangled and unknotted manner, i.e., in a bunched-up, readily separable mass, as will be described below. A curved, chevron or V-shaped notch 30 for the filament is partially cut into at or adjacent to at least one of the seals at a filament end, but does not extend completely therethrough.

As shown, a notch is cut into side seal 26a of package 20 of FIG. 1. The notch is so placed that the filament to be extracted from its package is positioned between the notch and the adjacent edge of the package, e.g., that edge which encompasses top seal 26d of package 20 of FIG. 1.

It is preferred that the notch be configured to encourage a directed tearing of the package across the filament. Thus, as an aid to the person opening the package, the notch may be defined by a first cut 30a and a second cut 30b both of which can be pointed in the direction in which the package is to be torn. However, this directing is not required; the notch only is a beginning point for tearing the package open.

Figure 2:
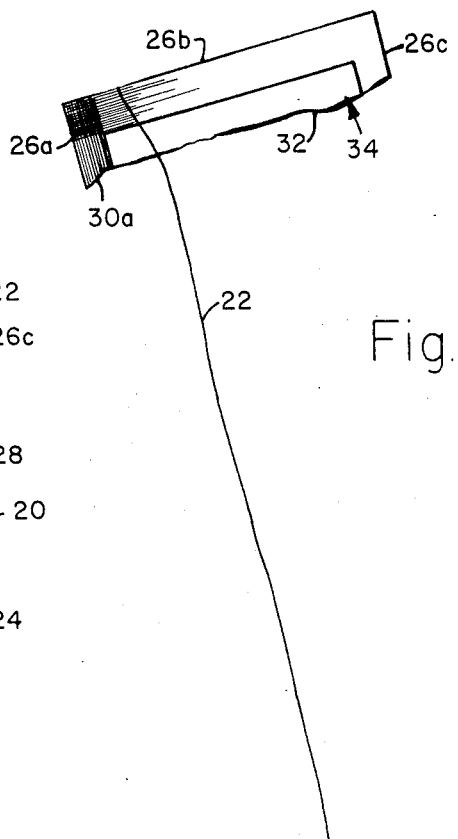
FIG. 2 illustrative of the opening of the package depicted in FIG. 1, and the drawing of the flaccid item therefrom in an untangled and unknotted manner with the aid of a segment of the package operating as a handle.

Such directional tearing is shown in FIG. 2, in which the tear in package 20 is denoted by indicium 32 and extends parallel to top seal 26b from side 26a to side 26c to form an end segment 34. If desired, the tear may extend diagonally from side 26a to top 26b to form a corner segment. In either case, the segment, e.g., end segment 34, entraps a filament end portion 22b, so that the package segment operates as a handle by which bunched-up portion 22a of the filament can be withdrawn easily and in an untangled and unknotted manner from the package.

Figure 3:
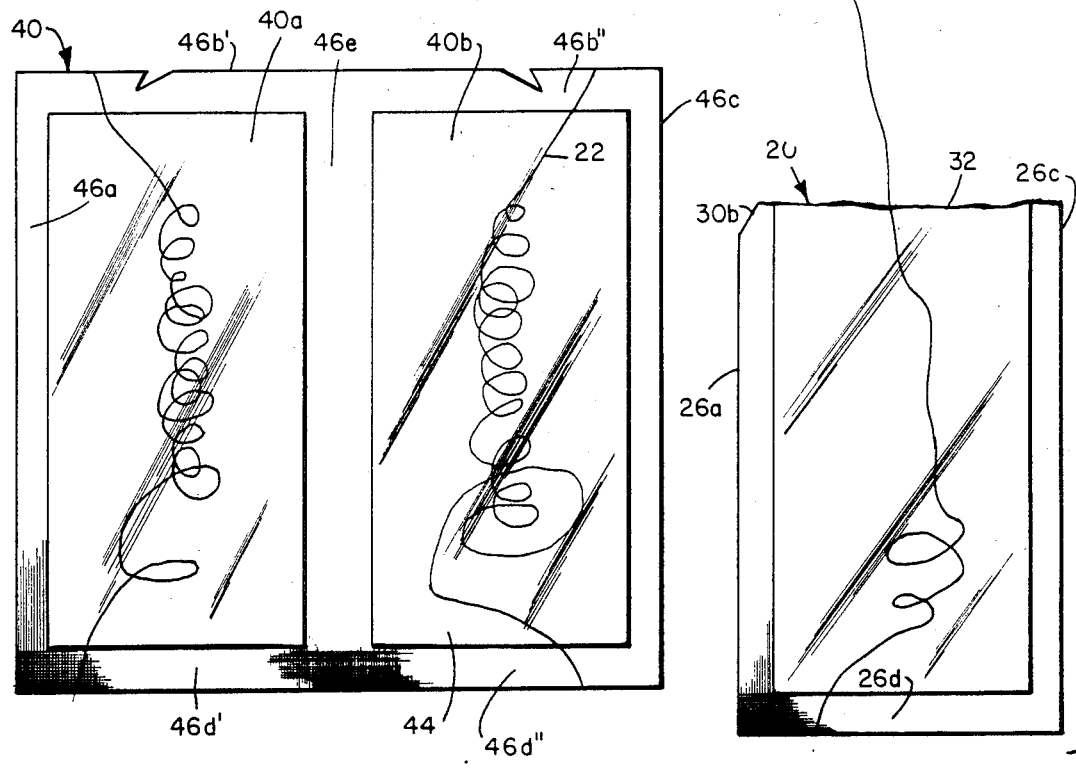
FIG. 3 shows another package configuration formed in accordance with a second embodiment of the present invention, in which a pair of flaccid items are sealed within separate enclosures within a single package.

A double package 40, similar to package 20 of FIG. 1, is shown in FIG. 3. In this embodiment, package 40 comprises a pair of sealed enclosures 40a and 40b, each containing a flaccid item 22 formed like the flaccid item of FIG. 1. Package 40 comprises a pair of flat walls 44 which are peripherally sealed to form a side 46a, a pair of top seals 46b' and 46b', a second side seal 46c, a pair of bottom seals 46d' and 46d', and an additional separating seal 46e intermediate side seals 46a and 46c.

Separating seal 46e is characterized as preferably encompassing an enlarged, continuously sealed area which may be centrally perforated to enable easy separation of enclosure 40a from enclosure 40b. Thus, individual sterility can be provided between the two enclosures and enables one to be opened without affecting the other; however, such a perforated seal area may be dispensed with if separation is not desired.

Packages 20 and 40 may be manufactured by the mechanism illustrated in FIG. 4 and the process steps associated therewith as illustrated in FIGS. 7-9. The arrangement uses basically standard packaging machinery, which is modified with the addition of novel filament feeding devices and relative movements among the several mechanical elements.

The packaging instrumentation includes two rolls or sources 50a and 50b of two films of wrapping material 52a and 52b, each of which may comprise either a single layer of polyethylene or a laminate of an inner layer of polyethylene and an outer layer of any suitable material, such as of paper or aluminum or any other materials or combinations as previously suggested. Polyethylene is preferred because it is easily heat-sealable and forms a secure and sanitary package. The outer layer is selected for decorative, message bearing and related or other reasons.

Films of wrapping material 52a and 52b are guided over rollers 53 for enabling them to be fed within a sealing mechanism 54 comprising mating halves 54a and 54b. Each half includes a pair of vertical, parallelly extending contactable faces separated by a vertical channel. The mating channels form a vertically extending tubular recess 56. The contactable faces of the mating halves may have interfitting ridges and grooves so that, when sealing mechanism 54 is heated and wrapping material films 52a and 52b are pressed between the vertically extending faces, the entrapped inner layer from the two films of wrapping material are sealed together at their edges but not at their centers, as permitted by recess 56 to form side seals, such as side seals 26a and 26c of FIG. 1.

Positioned below sealing mechanism 54 is a holder 58 comprising a pair of holder halves 58a and 58b, which include resilient pads 60 of elastomeric material. The halves are movable towards and away from one another to enable pads 60 to press against and hold the pouch.

Sealing mechanism 54 and holder 58 are connected by a coupling 62 which moves respective sealing halves 54a and 54b and holder halves 58a and 58b towards and away from one another, as represented by double-headed arrow line 64, and up and down in unison, as represented by double-headed arrow line 66.

A second sealing mechanism 68 comprises sealing halves 68a and 68b which are disposed to move only towards and away from one another, as represented by double-headed arrow lines 71. Each half includes a horizontally disposed sealing surface 70 which, when heated and pressing films 52a and 52b together, simultaneously form top and bottom seals, such as seals 26b and 26d of FIG. 1, but of successive packages, as will be better understood with the description of the steps associated with FIGS. 7-9.

A holding and cutting mechanism 72 is positioned below horizontally sealing mechanism 68 and holder 58. The holding and cutting mechanism includes a pair of holder halves 72a and 72b and a pair 74 of knife edges 74a and 74b, respectively attached thereto. The holding and cutting mechanism halves are constrained to move towards and away from one another as represented by double-headed arrow lines 76. Thus, when the halves move towards one another to grip a section of completed packages still attached to other packages, some of which are still in process of completion, knife edges 72a and 72b separate the lowermost package from the remaining packages.

In the packages of FIGS. 1 and 3, flaccid item 22, which is illustrated in FIG. 4 et seq. as a filament such as of dental floss, is supplied from one or more spools or bobbins 78 as a continuous, uncut length, which is extended over a guiding roller 80 into a feeding mechanism 82. The feeding mechanism comprises a feed tube 84 and a tubular mandrel 86, which are concentric and relatively movable with respect to one another. Preferably, however, feed tube 84 is movable and mandrel 86 is fixed to a support 88. Recess 56 of sealing mechanism 54 is wider than mandrel 86 and, therefore, extends about and preferably is not in contact with the mandrel. A spring 90, surrounding the feed tube, is compressed between support 88 and a collar 92 affixed to the upper end of feed tube 84, to absorb any shocks in the feeding mechanism during operation.

As best shown in FIGS. 5 and 6, feed tube 84 is terminated at its end 94 by a piston 96. The piston is bonded, threaded or otherwise affixed to feed tube 84 so that they move together within mandrel 68. Peripheral surface 96a of the piston has essentially the same dimension and configuration as inner surface 86a of mandrel 86 to provide a close interfit between the surfaces. To minimize friction, piston 96 is formed from polytetrafluoroethylene or an equivalent composition, while feed tube 84 and mandrel 86 are preferably metallic. e.g. of stainless steel or the like.

The sequence of process steps is illustrated in FIGS. 7-9, with further reference to a strip of packages in formation, designated by indicium 98. Strip 98 is shown in edge view in FIGS. 7-9 and in full side view in FIG. 10. In the latter Figure only a single completed entire package and a portion of another completed package, both identified by indicium 20', and a partially completed package 98a are shown, while the strip in FIGS. 7-9 may include a greater number than is illustrated in FIG. 10. Because the completed packages have not yet been separated from strip 98 through an enlarged sealed area 100 along dashed separation line 102 to separate sealed bottom 26d of one package from sealed top edge 26b of an adjacent package, the separated and non-separated packages are distinguished by indica 20 and 20', respectively.

As shown in FIG. 7, one or more packages 20' already have been completed and are in line for separation by cutter blades 74. Further, see also FIG. 10, a bunched-up amount 22a of filament 22 has been deposited into an open end within portion 98a of strip 98 and into compartment 28 upon the lowest travel of piston 96 at lower end 94 of feed tube 84.

Also, as shown in FIG. 7, vertically sealing halves 54a and 54b and holder halves 58a and 58b are in readiness to be moved towards one another, respectively, to form side seals 26a and 26c from web portions 52a and 52b and to press against the wrapping material and the bunched-up filament residing therein.

Heated sealer halves 54a and 54b and holder halves 58a and 58b are then respectively moved towards one another, as shown in FIG. 8, to seal the two films of the wrapping material together at their sides to form sealed side 26a and 26c. At the same time, holder halves 58a and 58b grip the wrapping material and filament portion 22a therebetween.

In the interval between the positions of the apparatus shown in FIGS. 8 and 9, coupling 62 moves both sealer 54 and holder 58 halves and strip 98 held thereby downwardly. This downward movement also draws measured lengths of filament 22 from bobbin 78 and of wrapping material films 52a and 52b from their sources 50a and 50b. After completion of the downward movement, combined holder and cutting mechanism 72 moves together both to grip strip 98 and to separate the lowermost completed package from the strip along a separation line 102. The sealer and holder halves 54a, 54b and 58a, 58b are then moved outwardly from strip 98.

Thereafter, as illustrated in FIG. 9 heated horizontally sealing halves 68a and 68b are moved into contact with the strip to form sealed area 100. During this time, piston 96 and feed tube 84 move up to their uppermost point to extend the measured length of filament 22 from end 94 of the feed tude. In the interval between the positions of the mechanism shown in FIGS. 9 and 7, sealer 54 and holder 58 move upwardly to their uppermost positions, and feed tube 84 moves downwardly to enable piston 96 to bunch up the previously straight filament and push filament portion 22a from the end of mandrel 86 and into compartment 28 of strip portion 98a.

Although the invention has been described with respect to particular embodiments thereof, it should be realized that various changes and modifications may be made therein without departing from the spirit and scope of the invention.

What is claimed is:

1. a packaging system for containing segments of a flaccid item comprising a length of tubular material, seals spaced from one another extending along the length of said tubular material and thus dividing said tubular material into a plurality of sealed compartments, and an uncut continuous length of said flaccid item extending through and within said tubular material and both sealed within said seals and contained within said sealed compartments, and tearing means disposed in the periphery of each sealed compartment for tearing across the compartment to dispense an end of the flaccid item without entanglement.

2. A packaging system according to claim 1 in which each of said seals extend sufficiently between adjacent ones of said compartments to enable said tubular material and said flaccid item sealed therewithin to be separated wholly within said seals and to maintain the sealed integrity of said compartment and said flaccid item contained therewithin.

3. A packaging system according to claim 2 in which said flaccid item comprises a filament.

4. A packaging system according to claim 3 in which said filament comprises dental floss.

5. A packaging system according to claim 2 in which said tubular material comprises heat sealable material, and said seals comprise locally heat-sealed portions of said tubular material.

6. A packaging system according to claim 5 in which said tubular material comprises at least one strip, and at least one sealed portion extending lengthwise of said tubular material and generally perpendicular to said spaced seals.

7. A packaging system according to claim 5 in which said tubular material comprises at least two strips, and at least two parallelly extending sealed portions extending lengthwise of said tubular material and generally perpendicular to said spaced seals.

8. A packaging system according to claim 2 in which said tubular material comprises a walled structure having inner and outer surfaces, with heat-sealable material defining said inner surface, and said seals comprise locally heat-sealed portions of said tubular material inner surface.

9. A flaccid item dispensing package comprising:
a pair of peripherally sealed, superimposed sheets that define a compartment;
a continuous, untangled, flaccid item having an intermediate portion terminating in opposite end portions, with the intermediate portion being disposed within said compartment and the opposite end portions being disposed within and secured by said peripheral seal at first and second positions; and
tearing means for tearing across said package to dispense an end of the flaccid item without entanglement.

10. A flaccid item dispensing package according to claim 9 in which said flaccid item intermediate portion disposed within said compartment has a bunched-up length which is greater than any internal linear dimension of said compartment.

11. A flaccid item dispensing package according to claim 10 in which said tearing means is positioned substantially adjacent to one of the end portions of the flaccid item to enable the removal of a package segment incorporating said one end portion of said flaccid item whereby said package segment acts as a handle for the untangled removal of said flaccid item from said compartment.

12. A flaccid item dispensing package according to claim 11 in which said package has a rectangular configuration, and said tearing means comprises a notch extending partially into said peripheral seal, and said segment comprises a corner of said package.

13. A flaccid item dispensing package according to claim 12 in which said notch comprises a chevron cut pointing in the direction of separation of said segment from said package.

14. A flaccid item dispensing package according to claim 11 in which said sheets include interfaces of heat-sealable material and outerfaces with said interfaces being heat-sealed within the area of the peripheral seal.

15. A flaccid item dispensing package according to claim 14 in which said outerface of at least one of said sheets comprises paper, plastic or aluminum foil.

16. A flaccid item dispensing package according to claim 14 in which said flaccid item comprises a filament of natural fiber, synthetic fiber, metallic wire or combinations thereof.

17. A flaccid item dispensing package according to claim 14 in which said flaccid item comprises dental floss.

* * * * *